US00PP13576P3

(12) United States Plant Patent
Bunnik

(10) Patent No.: US PP13,576 P3
(45) Date of Patent: Feb. 18, 2003

(54) GUZMANIA PLANT NAMED 'DEPLATIMA'

(76) Inventor: Ronald Bunnik, Hoefslag 3, 2641 ZZ Pijnacker (NL)

( * ) Notice: Subject to any disclaimer, the term of this patent is extended or adjusted under 35 U.S.C. 154(b) by 0 days.

(21) Appl. No.: 09/983,450

(22) Filed: Oct. 24, 2001

(65) Prior Publication Data

US 2002/0148027 P1 Oct. 10, 2002

(30) Foreign Application Priority Data

Apr. 5, 2001 (EP) ..... 2001/0627

(51) Int. Cl.[7] ..... A01H 5/00

(52) U.S. Cl. ..... Plt./371

(58) Field of Search ..... Plt./371

*Primary Examiner*—Kent L. Bell

(74) *Attorney, Agent, or Firm*—Foley & Lardner

(57) ABSTRACT

A new and distinct Guzmania plant named 'Deplatima' characterized by its big inflorescence size, red scape bracts with green tips, wide leaves and upright growth habit.

2 Drawing Sheets

LATIN NAME OF THE GENUS AND SPECIES OF THE PLANT CLAIMED

*Guzmania hybrid.*

VARIETY DENOMINATION

'Deplatima'.

BACKGROUND OF THE INVENTION

The present invention comprises a new and distinct cultivar of Guzmania plant, hereinafter referred to by the cultivar name 'Deplatima'. The genus Guzmania is a member of the family Bromeliaceae.

Guzmania comprise a genus of over 100 species of herbaceous evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania is generally from the yellow through orange but may also include flame red and red-purple. White or yellow, tubular, three petalled flowers may also appear on a stem or within the leaf rosette but are usually short lived.

Guzmania may be advantageously grown as potted plants for greenhouse or home use. Desirably the plants are shaded from direct sunlight during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots which are detached from the mother plant, and may be grown in an appropriate soil or bark mixture.

The new cultivar 'Deplatima' is the product of a planned breeding program originated by the inventor Ronald Bunnik in 1992, in Pijnacker, The Netherlands. The female and male parents are unknown Guzmania varieties. The selection comprising the new variety was chosen after commencement of flowering in 1993.

The new cultivar was asexually propagated by tissue culture in November 1995, by Kwekerij Sidaco BV in Nootdorp, The Netherlands. Continuous asexual propagation has demonstrated that the combination of characteristics as herein disclosed for the new cultivar 'Deplatima' are firmly fixed, reproduce true to type and are retained through successive generations of asexual reproduction.

BRIEF DESCRIPTION OF THE INVENTION

The following traits have been repeatedly observed and are determined to be basic characteristics of 'Deplatima' which in combination distinguish this Guzmania as a new and distinct cultivar:

1. Big inflorescence size;
2. Red scape bracts with green tips;
3. Wide leaves; and
4. Upright growth habit.

'Deplatima' has not been observed under all possible environmental conditions. The phenotype of the new cultivar may vary significantly with variations in environment such as temperature, light intensity, and day length without any change in genotype.

Of the many commercial cultivars known to the present inventor, the most similar in comparison to 'Deplatima' is the cultivar 'Tutti Frutti' (U.S. Plant Pat. No. 8,717). In comparison to 'Tutti Frutti', the inflorescence of 'Deplatima' is smaller, much redder and is flatter and shorter. The leaves of 'Deplatima' are wider than the leaves of 'Tutti Frutti'.

BRIEF DESCRIPTION OF THE DRAWINGS

The photographic illustrations show a 19-month-old 'Deplatima' plant grown in an 11 cm pot, following growth under appropriate growing conditions, with colors being as true as possible with illustrations of this type.

The first drawing depicts a typical plant of 'Deplatima' from a top view perspective.

The second drawing depicts a close-up view of the inflorescence and foliage of 'Deplatima'.

DETAILED BOTANICAL DESCRIPTION

The following observations, measurements and values describe 19 month old plants grown in 11 cm containers in Evergem, Belgium, under greenhouse conditions which closely approximate those generally used in horticultural practice.

'Deplatima' is grown in a commercial greenhouse under 21 degrees Celsius day and night. No artificial lighting or photoperiodic treatments are conducted but 'Deplatima' is forced into flowering by adding acetylene. Highest temperature resistance is 40 degrees Celsius, the lowest 5 degrees Celsius. Direct sunlight has to be avoided because it causes burning of the leaves. The following fertilizer is added: 1 part nitrogen, 0.5 parts phosphor. 3 parts Kalium and 0.2 parts Magnesium. Water should not contain to much salts. From the start of tissue culture it takes five years to produce a commercial plant. The amount of time needed to produce an inflorescence depends on the amount of acetylene is added. The inflorescences have a tenability of up to six months depending on the environment they are grown and kept in.

Color references are made to The Royal Horticultural Society Colour Chart (R.H.S.), except where general colors of ordinary significance are used.

Propagation: Tissue culture.

Plant:

*Form.*—Upright, leaves in basal rosette.

*Height.*—Average 40 cm.

*Diameter.*—Average 70 cm.

*Growth habit.*—Upright, growth moderate.

Foliage:

*Size.*—Leaves have an average length of 41 cm and an average width of 5.5 cm (measured at the middle of a leaf).

*Shape.*—Broad linear, tips acute.

*Margin.*—Entire.

*Surface texture.*—Smooth, glossy.

*Color.*—Leaf color upper side; dark green to dark yellow-green; in between RHS 139A and RHS 147A, but slightly darker. Leaf color under side yellow-green, RHS 147A, young leaves dark greyed-purple at underside, RHS 186C; older leaves sometimes striped greyed-purple at the base as well, between RHS 187B and RHS 187C.

Bracts:

*General shape/arrangement.*—Broad lanceolate, arranged alternately, tips arranged horizontally.

*Scape bracts.*—Number: Average 10. Length: Average 13.5 cm. Width: Average 3.9 cm. Margin: Entire. Apex: Acute. Color: Upper side red RHS 46A; upper half to tips yellow-green RHS 147A; under side greyed-purple RHS 185A with yellow-green tips RHS 147A. Texture: Smooth, glossy.

*Primary bracts.*—Number: Average 10. Length: Average 10.7 cm. Width: Average 4.1 cm. Margin: Entire. Apex: Acute. Color: Upper side red RHS 45A, with red RHS 46A to brown RHS 200A tips; under side red RHS 53B with red RHS 46A to brown RHS 200A tips. Texture: Smooth, glossy.

*Floral bracts.*—Number: Average 9. Length: Average 5.6 cm. Width: Average 1.8 cm. Margin: Entire. Apex: Apiculate. Color: Upper side red RHS 53B to between RHS 44B and RHS 44C; red RHS 46A; under side red between RHS 53B and RHS 53C, with red RHS 46A and orange RHS N25A tips. Texture: Smooth, not glossy.

Inflorescence:

*Borne.*—Solitary upright inflorescence, only very few inflorescences appear; each inflorescence consists of approximately 9 flowers.

*Inflorescence length.*—Average 2.6 cm.

*Individual flowers.*—Average length 2.5 cm, average with 0.5 cm.

*Perianth.*—One large petal, broad lanceolate, slightly folded, average length 4.3 cm, average width 9 mm, outer color yellow-green between RHS 151D and RHS 151A; base lighter between RHS 154C and 154D. Calyx: Average length 2.5 cm, white in color, RHS 151D (both surfaces). Corolla: Average length 1 cm, yellow in color, RHS 12A (both surfaces).

*Time of blooming.*—Summer.

*Duration of inflorescence.*—More than one month.

Reproductive organs:

*Ovary.*—Ovate, average length 6 mm, average width 3.5 mm, light yellow-green in color, RHS 150D to green-white, RHS 157A. Ovary ribbed axially, due to three locules.

*Style.*—1 per flower, average length 1.2 cm, white in color, RHS155C, stigma not deeply cleft in two parts, approximately 2 mm long, white in color RHS 155C.

*Stamens.*—Average 6, basifixed, shaped narrow sagittate, average length 6 mm, average width 1 mm, color green-white; RHS 157A.

*Pollen.*—Small quantity, light yellow in color, closest to RHS 4C.

Roots: Thin, very well-branched, strong to moderately strong, color greyed-orange; RHS 165A.

Seed characteristics: No fruits or seeds observed to date.

Pest/disease resistance/susceptibility: No observations to date.

I claim:

1. A new and distinct Guzmania plant named 'Deplatima', substantially as illustrated and described herein.

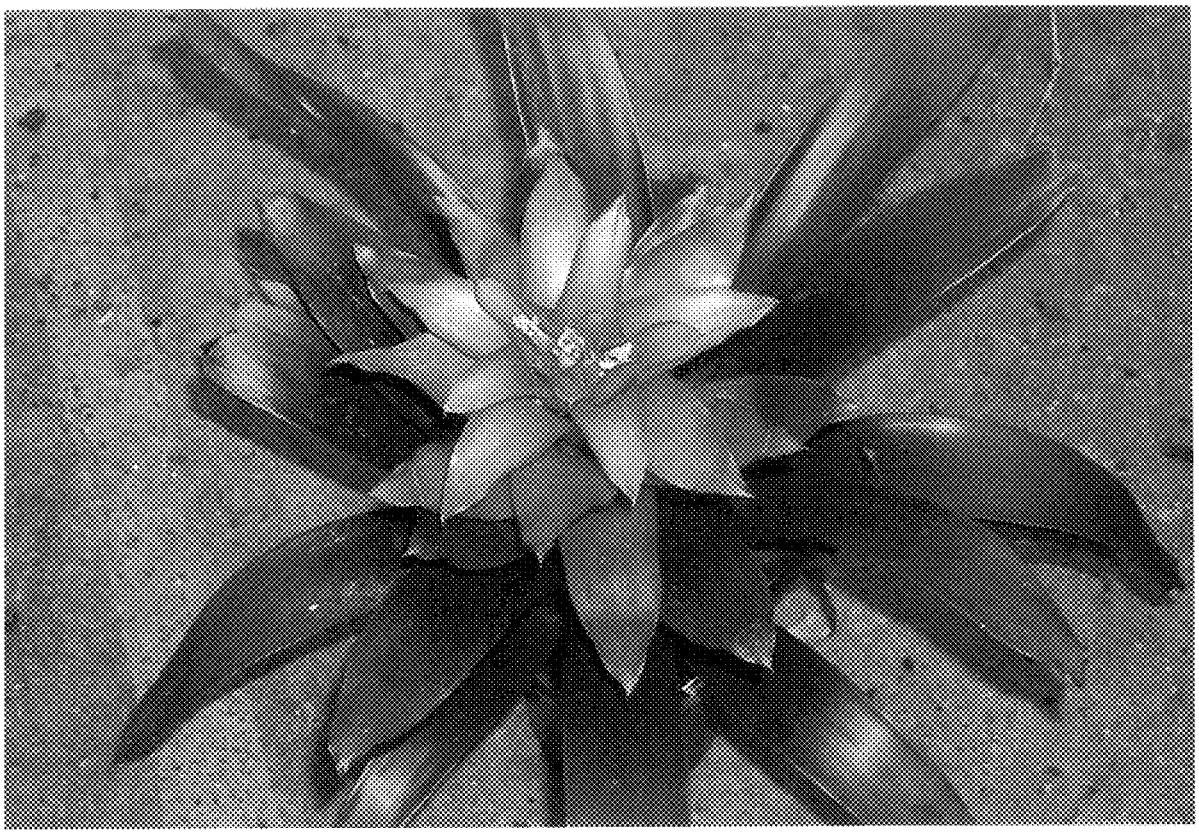

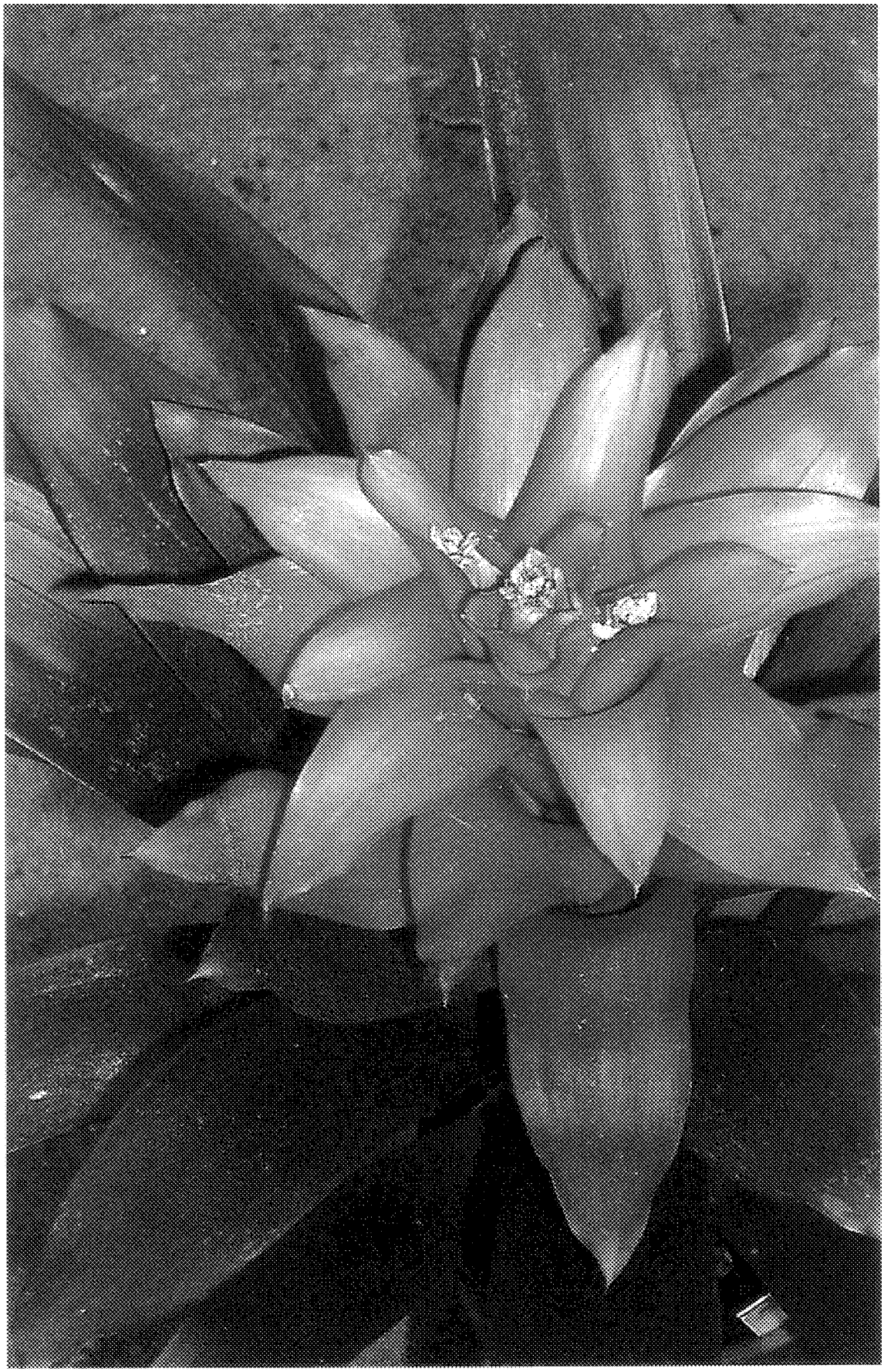

* * * * *